(12) United States Patent
O'Kelly

(10) Patent No.: US 7,319,902 B2
(45) Date of Patent: Jan. 15, 2008

(54) METHOD AND DEVICE FOR ELECTROCHEMICAL REJUVENATION OF SKIN AND UNDERLYING TISSUE, AND MUSCLE BUILDING

(76) Inventor: Gregory O'Kelly, 392 Pismo St., San Luis Obispo, CA (US) 93401

( * ) Notice: Subject to any disclaimer, the term of this patent is extended or adjusted under 35 U.S.C. 154(b) by 399 days.

(21) Appl. No.: 11/126,018

(22) Filed: May 9, 2005

(65) Prior Publication Data

US 2006/0253165 A1  Nov. 9, 2006

(51) Int. Cl.
*A61N 1/32* (2006.01)
*A61N 1/30* (2006.01)
*A61M 1/44* (2006.01)

(52) U.S. Cl. ............... 607/50; 607/48; 607/72
(58) Field of Classification Search ............ 607/1, 607/2, 48, 49, 50–52, 72
See application file for complete search history.

(56) References Cited

U.S. PATENT DOCUMENTS

| | | | |
|---|---|---|---|
| 4,326,534 A | 4/1982 | Axelgaard | |
| 4,342,317 A | 8/1982 | Axelgaard | |
| 4,408,609 A | 10/1983 | Axelgaard | |
| 4,580,570 A * | 4/1986 | Sarrell et al. | 607/63 |
| 4,595,010 A | 6/1986 | Radke | |
| 4,712,558 A | 12/1987 | Kidd et al. | |
| 4,811,742 A | 3/1989 | Hassel et al. | |
| 4,832,033 A | 5/1989 | Maher et al. | |
| 4,838,272 A | 6/1989 | Lieber | |
| 5,097,833 A | 3/1992 | Campos | |
| 5,433,737 A | 7/1995 | Aimone | |
| 5,507,788 A | 4/1996 | Lieber | |
| 5,678,535 A | 10/1997 | DiMarco | |
| 5,871,534 A | 2/1999 | Messick et al. | |
| 5,911,218 A | 6/1999 | DiMarco | |
| 5,974,342 A | 10/1999 | Petrofsky | |
| 6,330,476 B1 | 12/2001 | Ben-Haim et al. | |
| 6,363,279 B1 | 3/2002 | Ben-Haim et al. | |
| 2003/0163163 A1* | 8/2003 | Orton | 607/3 |
| 2004/0138708 A1* | 7/2004 | Tucek | 607/2 |
| 2005/0234525 A1* | 10/2005 | Phillips | 607/68 |

OTHER PUBLICATIONS

Fairchild Semiconductor, CD4538BC Dual Precision Monostable, 11 pages, Oct. 1987, Revised 2002.

* cited by examiner

*Primary Examiner*—Carl Layno
*Assistant Examiner*—Tammie K. Heller
(74) *Attorney, Agent, or Firm*—Nixon Peabody LLP

(57) ABSTRACT

A method and device are disclosed for using electrochemistry to rejuvenate skin and underlying tissue and to build and strengthen muscles by applying pulses of DC electrical charge, at a duration in the range of about 0.2 to about 1 millisecond and a variable frequency in the range of about 400 to about 1200 Hertz, to the skin immersed into an container of an electrolyte by means of an anode immersed in or connected to the container to cause the muscle to twitch or only slightly contract with each pulse. The DC is applied at variable current amplitude of from about 1 to about 50 milliamperes, and a voltage in the range of about 50 to about 120 volts.

29 Claims, 3 Drawing Sheets ated herein

METHOD AND DEVICE FOR ELECTROCHEMICAL REJUVENATION OF SKIN AND UNDERLYING TISSUE, AND MUSCLE BUILDING

This application is related to and contains common subject matter with U.S. Ser. No. 10/301,048 filed Nov. 20, 2002; now U.S. Pat. No. 6,856,837 issued Feb. 15, 2005 (the '837 patent), the contents of which are incorporated herein by reference.

FIELD OF INVENTION

The present invention relates to a method and device for the rejuvenation of skin and underlying tissue and for strengthening and building muscle. More particularly, the invention relates to using electrical impulses for the rejuvenation of skin and underlying tissue and for strengthening and building muscle through the use of electrochemistry.

BACKGROUND OF THE INVENTION

All cells of an organism need an external source of chemical energy so that they may conduct chemical activity involving self-maintenance, replication, and the synthesis of proteins and enzymes. This is the nature of metabolism. Metabolic energy is quantized in the form of the electron. Electrons are passed in oxidation-reduction reactions, i.e., electrochemistry, two chemical reactions involving the exchange of electrons. It is presented in the term $\mu$ in the equation $P=W^{(4\mu-1/4\mu)}$, where P is metabolic rate, and, by implication, the healthy functioning of the cell or the organism; W is body or cell size; and $\mu$ is metabolic efficiency, the ratio of rate of ATP (Adenosine Triphosphate) synthesis within the cell to the rate of electron flow from outside energy sources. In other words, metabolic efficiency is just the efficiency with which electron flow from outside oxidative reactions is able to trigger reduction reactions within the cell in the form of the synthesis of the energy storehouse molecule, ATP. The use of externally introduced electrical fields to trigger ATP synthesis in cells in vitro has been experimentally verified and reported in the literature on the subject.

The cells of a multicellular organism with a nervous system receive energy harvested from food sources through the delivery of nervous system trophism. This trophism is of an electrochemical character such that the oxidative digestion of food in the gut or alimentary canal triggers the reductive synthesis of ATP in the neurons of the nervous system which, in turn, discharge this energy down a nerve fiber to a somatic structure of the body on the other side of a peripheral, chemical synapse at the nerve fiber terminal, e.g., muscle, organ, and gland. From this synapse grows a system of electrical synapses that conduct the energy arriving from the nervous system to the individual cell of the somatic structure (muscle or organ or gland), except for the skin cells which are not reached by the flow of such nervous trophism, though they may be supplied with nutrients from the vascular system. Nerve fibers do not extend to the skin, and the circulatory system does not deliver energy in the form of electrons or metabolic energy to skin cells. In general the health of the skin is dependent upon the health of underlying tissue.

There is a need for the electrochemical rejuvenation of the skin that delivers metabolic energy to the skin to assist in its self-repair and maintenance by triggering the synthesis of ATP in underlying tissue of the skin cells.

SUMMARY OF THE INVENTION

The present invention is directed to the delivery of electrons/metabolic energy to trigger ATP synthesis in the skin cells through the use of electrochemistry by means of an anode of direct current (DC) discharged into a bath into which a body part is immersed. Depending upon the electrical pressure or voltage driving this discharge, the duration of exposure to this discharge, and the nature of the voltage waveform, the same delivery of metabolic energy can also penetrate deeply to supplement the metabolic energy of the cells there and to restore and build muscle and tissue underlying the skin.

The method of present invention uses electrochemistry to build and strengthen muscles and to energize skin cells by immersing a part of the anatomy to be treated into a container containing an electrolyte, connecting an anode plate in contact with the electrolyte to a power source, and generating pulses within the container at a current amplitude of from about 1 to about 50 milliamperes, a voltage in the range of about 50 to about 120 volts, a pulse duration in the range of about 0.2 to about 1 millisecond and at a frequency in the range of about 400 to about 1200 Hertz (referred to herein as the pulse rate).

One embodiment of a device, a pulse generator, for carrying out the method of the present invention includes the following elements:

a power supply that produces a power signal at a power output terminal, the power signal having a current amplitude range variable between about 1 to about 50 milliamperes, and a DC voltage range from about 50 to about 120 volts;

a pulse generating circuitry operably connected to the power supply that generates a pulse of variable duration in the range of about 0.2 to about 1 millisecond, and a pulse frequency in the range variable between about 400 to about 1200 Hertz;

a switching circuit that is coupled to receive the pulse signal having a switching output terminal, and in response to the pulse signal, the switching circuit operates to couple and uncouple the switching output terminal to a system ground;

a cathode having a first end that is detachably attached to the switching output terminal and a second end;

a battery whose anode is connected to the second end of the cathode and whose cathode is connected to a cathode plate;

a container containing an electrolyte; and an anode having a first end that is detachably attached to the power output terminal, and a second end that comprises an anode plate in contact with the electrolyte.

The anode plate of the device is either immersed in or connected to an electrically conductive container of electrolyte. The cathode of the battery to be drained is connected to a corrodible cathode plate that is preferably covered with an absorbent, wet cloth and brought into contact with the body by being placed against the body or placed in an electrolytic/ salt water solution into which the non-treated part of the anatomy is immersed. The oxidative corrosion of the battery reduces still further the corrosion of the cathode plate at the point of contact on the body. A limb or portion of the body to be treated is immersed in the water containing or contained by the anode, and the battery, preferably a low voltage DC battery, discharges through the power supply which in turn delivers the charge of pulsed, monophasic voltage to the body via the electrolyte.

The muscle is built and strengthened and the skin is energized using this system to deliver electrical charge between about 10 to about 50 milliamperes at an open circuit voltage of up to 120 volts for treatment times in the range of about 5 minutes to about 15 minutes.

BRIEF DESCRIPTION OF THE DRAWINGS

Further features and advantages will become apparent from the following and more particular description of the preferred embodiments of the invention, as illustrated in the accompanying drawings in which.

DETAILED DESCRIPTION OF THE INVENTION

The method and device of the present invention is an improvement of the method and device disclosed in the '837 patent directed solely to the building of muscle. In the present invention not only are the muscles built, but also the skin cells are energized through increased opening of the capillaries causing the nourishing of the skin and through triggering ATP synthesis in the skin cells. The '837 patent is directed to the electrochemical building of muscle by the stimulus from the anodic probe, a pulsed delivery of between 5 and 25 milliamperes at open circuit voltages up to 120 volts at frequencies around 1000 Hertz, delivered only to a small surface area overlying a neuromuscular junction, for a couple of seconds. This approach builds muscle, but limits the direct, positive benefits of such electrical field introduction to only small areas of the skin overlying neuromuscular junctions, and at such density that the skin could suffer if the exposure was too long. Though the skin would benefit by the improved blood flow to the skin resulting from restoration of tissue beneath, it would not directly benefit to any great extent from the triggering of ATP synthesis in large swaths of skin cells.

The method and device of the present invention improves upon that of the '837 patent in which an electrical charge is concentrated for a few seconds on a small spot on the body being treated to one in which longer treatment times are achieved and greater areas of the body are exposed at much lower concentration levels of charge. Because the same voltages needed to drive the amperage deeply into the body to build muscle is used, prolonged exposure times over a larger surface will result in the same or more electrical charge reaching the neuromuscular junction, thereby strengthening muscles immersed in the electrolyte/tap water, and energizing skin cells without causing burns or blistering on small spots, or muscle contractions.

Figure 1:
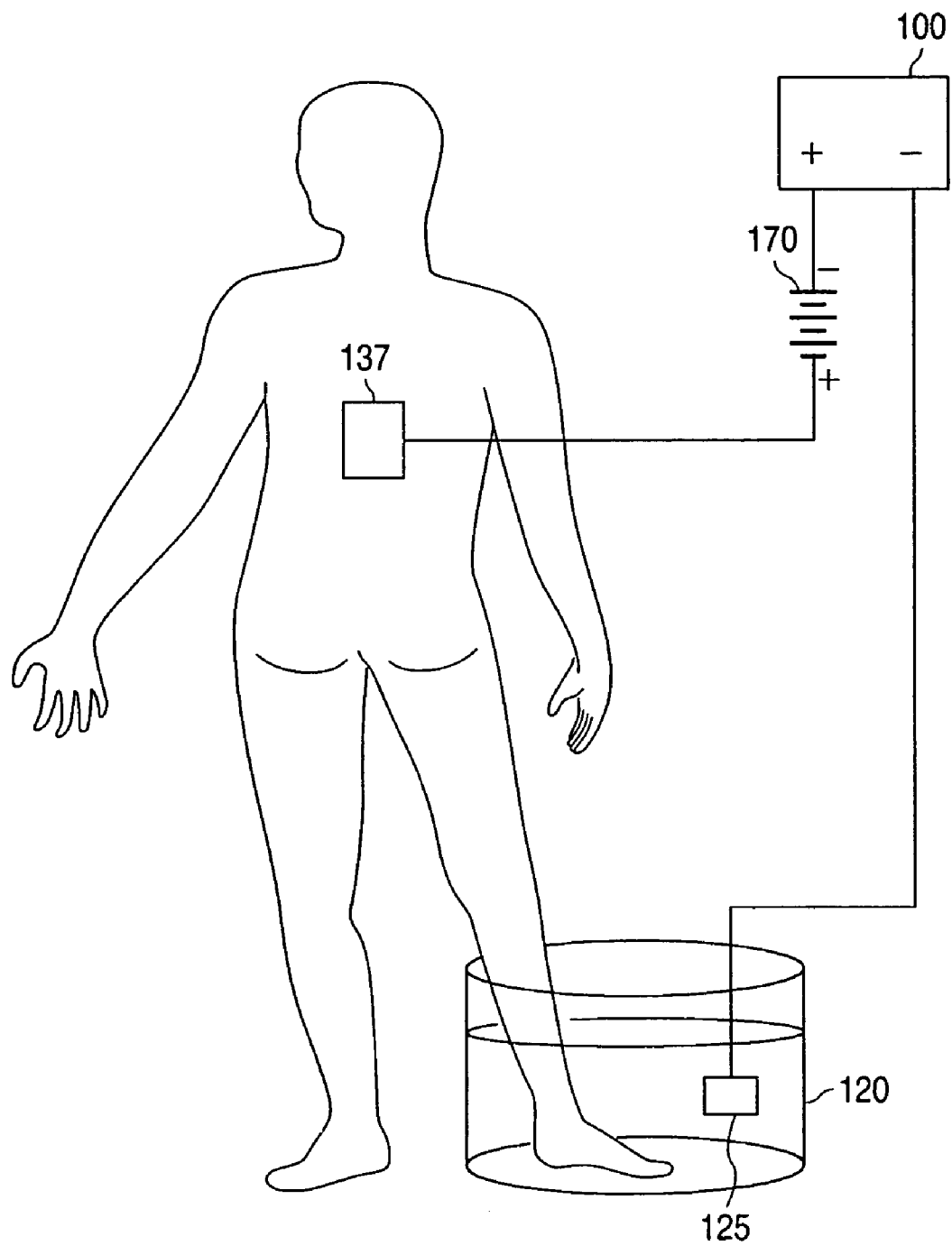
FIG. 1 is a block diagram of one embodiment of the present invention.

FIG. 1 shows pulse generating device 100 for generating pulses to stimulate a muscle's transverse tubule in accordance with one embodiment of the present invention. The stimulation carried along this tubule throughout the cell to trigger protein synthesis necessary for muscle building and muscle contraction is the same as that disclosed in the '837 patent, but is delivered in such a dispersed manner that it also triggers beneficial synthesis of ATP by the skin cells rather than causing them harm through powerful concentrations of electrical charge. The synthesis of ATP makes possible energy capture by the cell.

Device 100 generates a pulsed, monophasic voltage waveform of between about 50 and about 120 peak open circuit voltage and passes the voltage in the range of about 1 to 50 milliamperes of electrical current. The circuitry in device 100 shown in FIG. 2 allows the user to vary the frequency of the pulsing from between about 400 to about 1200 Hertz, at a pulse width not less than about 0.2 milliseconds and not more than about 1 millisecond, and to vary the amplitude of the rate of flow of current from 0 to 50 milliamperes.

A large container 120 is shown in FIG. 1 into which is placed tap water to serve as an electrolyte, preferably containing a teaspoon of salt or soda to reduce resistance to the flow of current in the water. The area of the body to be treated, e.g., foot, leg, hand, face, is immersed in container 120. A plate 125, preferably made of stainless steel is connected to the anode of device 100 and placed into container 120. A cathode plate 137 is connected to the cathode of battery 170 whose anode is connected to the cathode of device 100. Cathode plate 137 is made of a corrodible metal like iron or zinc, and that part of plate 137 that is to come in contact with the body preferably should equal or exceed 9 square inches in area and be covered by a wet, absorbent cloth.

In FIG. 1, battery 170 has its anode connected to the cathode of device 100, and its cathode is connected to cathode plate 137. Preferably, battery 170 should not be of a voltage greater than about 12 volts, and should be chosen for the ease with which it gives up current. In this regard a lead-acid or nickel-metal hydride battery is to be preferred, but an alkaline or nickel-cadmium battery will also work, of C or AA size.

With the area of the body to be treated immersed in the water in container 120, the user places the cathode plate 137 in contact with the body, and turns on the current from the device 100 at the lowest setting. The frequency and amplitude of the pulses provided by device 100 are increased and/or adjusted so that the user feels the current but it is not unpleasant. Cathode plate 137 is moved about the body while remaining in contact with the body so that the harsh effects of the cathode are distributed over a larger area than that of the cathode plate itself. The preferred treatment times vary from 5 to 15 minutes. If the user wants to cause muscle contractions the current strength may be increased to the point where muscle contractions can be triggered, and the frequency of the pulsing adjusted to where the contractions are the strongest. This is between about 800 and about 1000 Hertz, and may vary from one muscle to another. But muscle contractions are not needed for muscle to be strengthened using electrochemistry, and this is the advantage of this new invention.

The user should not introduce to or remove from container 120 the area to be treated unless current flow is terminated, otherwise reduced skin surface area in the water will experience a greater density of electrical charge as the limb is removed or inserted. Consequently, this will be painful to the user. At current strengths strong enough to trigger contractions in muscle at high densities on small surface areas, but which do not cause contractions when more skin surface area is immersed, the muscle will still be strengthened despite lack of contractions. This is the case if the area or muscle being treated is allowed to remain in the water for longer periods, e.g., for 10 to 15 minutes rather than 5 minutes.

Figure 2:
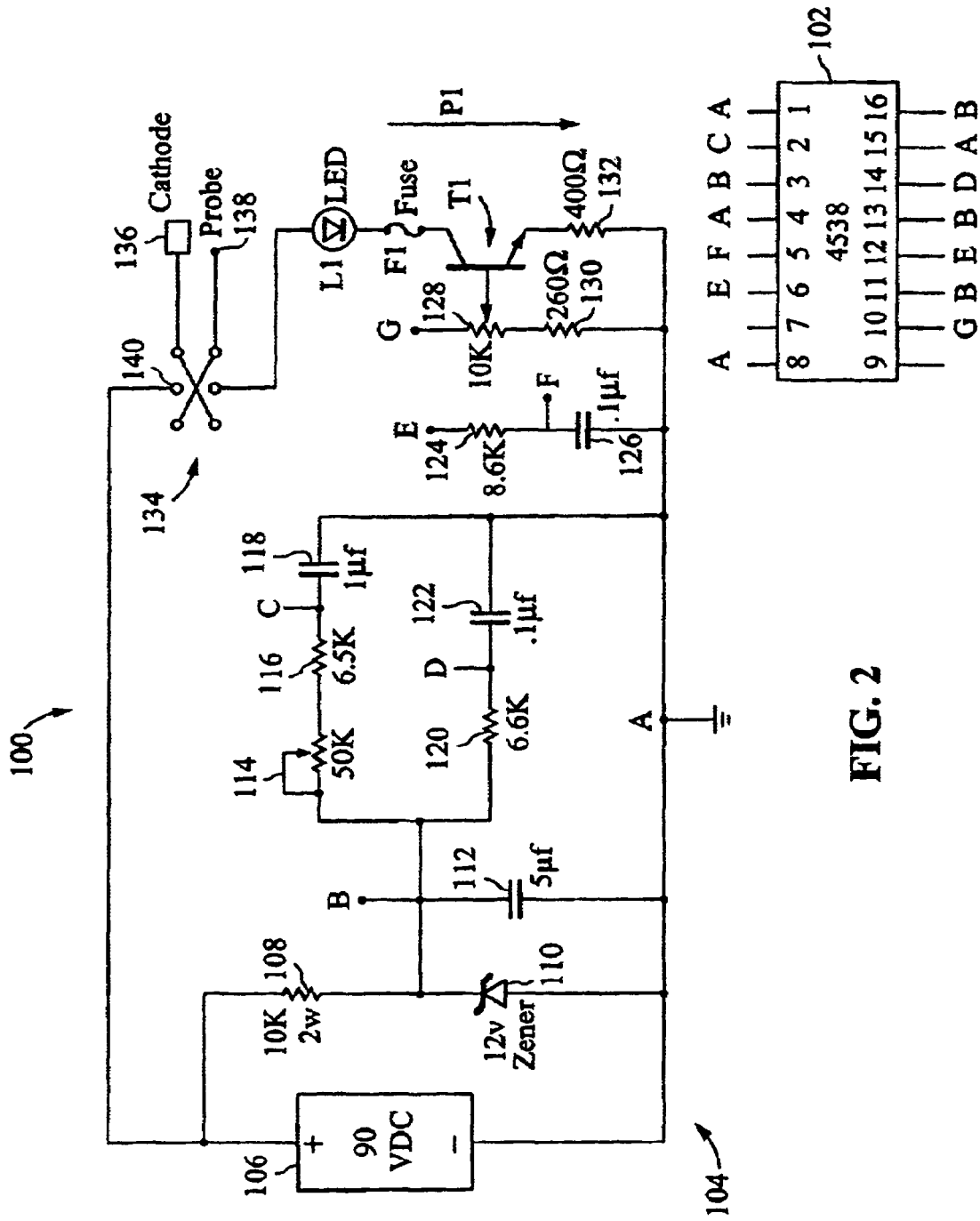
FIG. 2 is a block schematic diagram of one embodiment of the present invention shown in FIG. 1.

FIG. 2 shows a switching circuit 102 and associated pulse generating circuitry that is generally shown at 104 of device 100. The switching circuit is preferably a CMOS 4538 solid-state integrated circuit, as this allows for a constant pulse width over the possible frequency range. However, other switching circuits are suitable for use in other embodiments of the invention that rely upon a 555 timer circuit, a complete description of which is found in the '837 patent. The 555 timer circuit varies the pulse width with the frequency, the pulses being longer when the frequency is very low.

Device 100 includes a 90-volt DC power source 106 that has a positive output coupled to a power resistor 108 and a 12-volt zener diode 110. In a preferred embodiment, AC from a wall socket is transformed and rectified by a transformer/rectifier (not shown) to achieve the required DC voltage. A negative output of the power source 106 is coupled to a system ground at Node A of circuit 102. The power source 106 is used to generate a 12-volt DC signal at node B, which is coupled to a system ground through capacitor 112. Node B is also coupled to two timing circuits. The first timing circuit comprises potentiometer 114, resistor 116 and capacitor 118. A terminal (Node C) is defined at the coupling between the resistor 116 and the capacitor 118. The second timing circuit comprises resistor 120, which determines pulse width, capacitor 122, and a Node D terminal defined at the coupling between resistor 120 and capacitor 122. Capacitors 118 and 122 are also coupled to the system ground.

A Node E terminal is coupled to resistor 124, which in turn is coupled to capacitor 126 at Node F. Capacitor 126 is also coupled to the system ground. A Node G terminal is coupled to potentiometer 128 that is also coupled to resistor 130. The center wipe of the potentiometer 128 is connected to a base terminal of transistor T1. An emitter terminal of T1 is connected to resistor 132, and a collector terminal of T1 is connected to fuse F1, which is preferably a 0.3 amp fast blow fuse. Preferably transistor T1 is a Philips EGC 396 transistor or equivalent.

An LED (L1) is connected between the fuse F1 and a cross-connect 134. The cross-connect is coupled to a cathode terminal 136 and an anode or probe terminal 138. The cathode 136 preferably is connected to the anode of battery 170 and thence to cathode 137 shown in FIG. 1, or cathodic vessel 139 shown in FIG. 3. The cross-connect 134 is used to selectively connect the cathode and probe terminals to the circuit. The switching circuit 102 is an integrated circuit that is connected to the circuitry 140 according to the terminals indicated at each pin of the circuit 102. For example, pins 1, 4, 8, and 15 of the switching circuit are all connected to terminal Node A. Thus, the switching circuit 102 and the circuitry 104 operate together to generate pulses in accordance with the present invention.

During operation, 90 volts DC from the power source 106 appears at terminal 140 of the cross connect 134. Assuming the corroding cathode 137 and anode 125 shown in FIG. 1, or cathode 139 and anodic vessel 126 shown as an alternative embodiment in FIG. 2, are connected into the circuit, operation of the switching circuit 102 causes pulses to appear at Node G, which selectively activates transistor T1. T1 is "turned on," by connection of anode and cathode in the circuit. This occurs when the user applies cathode 137 to the skin not immersed in vessel 120 while simultaneously having another part of the body in anodic vessel 120 shown in FIG. 1. Alternatively, T1 is "turned on" when the user immerses some part of the body in cathodic vessel 139 while simultaneously having the part of the body to be treated immersed in anodic vessel 126 shown in FIG. 2. When T1 is "turned on," current can flow through path P1 shown in FIG. 3. An LED is provided to indicate when current is flowing through P1.

Figure 3:
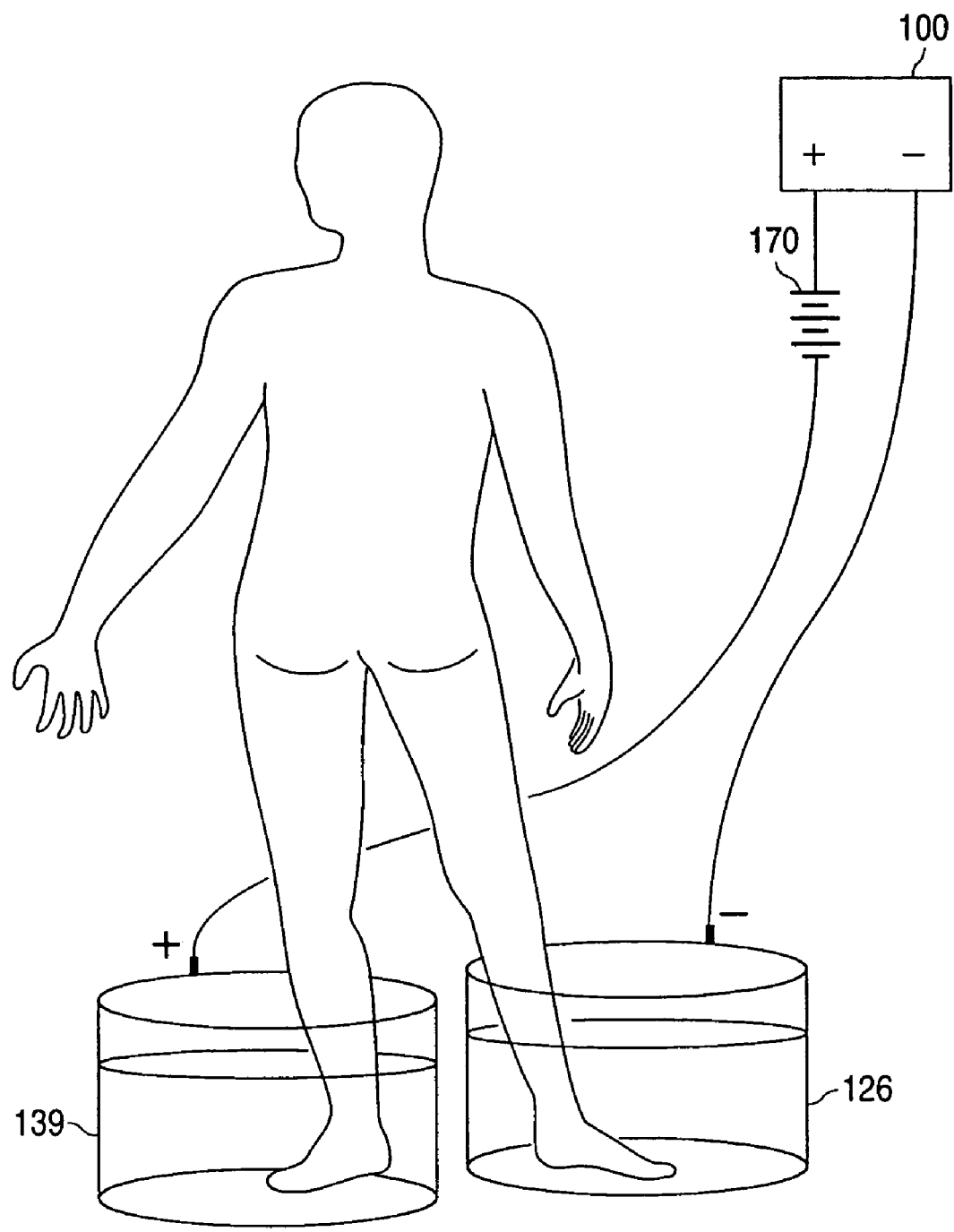
FIG. 3 is a block diagram of another embodiment of the present invention.

By adjusting the timing circuits, it is possible to achieve various pulse rates and current amplitudes as discussed in detail below. Particularly, this may be accomplished by adjusting potentiometers 114 and 128. Therefore, when cathode 136 and anode or ground 138 shown in FIG. 3 are connected by means of a user simultaneously being in contact with cathode 137 or immersed cathodic vessel 139 while having a body part immersed in the vessel 120 containing anode 125 or anodic vessel 126, pulses generated by the switch control circuit 102 control current flowing down path P1, and thereby energize the muscle cell's transverse tubule to build muscle and synthesize cellular ATP in accordance with the present invention. Immersion of a body part in the anodic vessel at a frequency between about 400 and about 1000 Hertz, with a pulse width of about 0.25 milliseconds, and a current strength variable preferably between about 5 and about 50 milliamperes, is sufficient to overload any and all muscles of the body immersed for over 10 minutes without causing muscle contractions, and only 5 minutes if the current is strong enough to cause contractions.

In FIG. 3 is shown an alternate embodiment of the method. In this embodiment the anode container 126 is itself electrically conductive. Skin should not make contact with the dry metal, but can come into contact with the metal underwater. In this embodiment the cathode plate is replaced by a container 139 which is also electrically conductive. This arrangement allows for the harsh effects of the cathode to be distributed over a wider area without having to trouble with moving the cathode plate 137 constantly over the body. Container 139 can be either made of a corrodible material, in which case it will need to be cleaned of oxidized metal from time to time, or it can be made of stainless steel. Alternatively, vessel 139 may be made of a non-conductive and contain the corroding cathode 137 shown in FIG. 1.

An example of the use of this method of strengthening muscle and rejuvenating skin has been demonstrated by regularly immersing the user's face and front of the head into container 120 while the cathode plate 137 was passed over the user's abdomen, while always maintaining plate 137 in contact with the user's skin. The treatment time was between eight and ten minutes at a current amplitude setting which, if delivered in accordance with the method of the '837 patent, i.e., via a transcutaneous electrode, would have been too painful to sustain even for a second. The user was able to maintain normal breathing during this period through the use of a snorkel.

Without departing from the spirit and scope of this invention, one of ordinary skill in the art can make various changes and modifications to the method of the present invention to adapt it to various usages and conditions. As such, these changes and modifications are properly, equitably, and intended to be, within the full range of equivalents of the following claims.

What is claimed is:

1. A method of building muscle and energizing skin cells through the use of electrochemistry, comprising immersing a part of the anatomy to be treated into a container containing an electrolyte, connecting an anode plate in contact with the electrolyte to a source of direct current power, and for generating pulses within the container at a current amplitude of from about 1 to about 50 milliamperes, a voltage in the range of about 50 to about 120 volts, a pulse duration in the range of about 0.2 to about 1 millisecond and at a frequency in the range of about 400 to about 1200 Hertz.

2. The method of claim 1, wherein the current amplitude is in the range of about 10 to about 20 milliamperes for treatment times in the range of about 5 minutes to about 15 minutes.

3. The method of claim 2, wherein the voltage is in the range of about 50 and 120 peak open circuit voltage.

4. The method of claim 1, wherein the voltage is generated in a pulsed monophasic waveform.

5. The method of claim 4, wherein the anode plate is immersed in the electrolyte.

6. The method of claim 5, wherein a cathode plate is placed in contact with another part of the anatomy outside of the electrolyte.

7. The method of claim 6, wherein the source of direct current power has an anode that is connected to anode plate and a cathode connected to an anode of a battery, and the cathode plate is connected to a cathode of the battery.

8. The method of claim 7, wherein the cathode plate is greater than 9 square inches in area, made of an easily corrodible metal, and covered with a wet, absorbent cloth.

9. The method of claim 8, wherein the source of direct current power is a pulse generator that generates a pulsed, monophasic voltage.

10. The method of claim 9, wherein while the part of the anatomy being treated is immersed in the electrolyte through which the anode acts, and the cathode plate is moved over the surface of the part of the anatomy outside of the electrolyte.

11. The method of claim 10 wherein the battery is designed to readily pass a charge at a voltage of no greater than about 12 volts.

12. The method of claim 11 wherein the battery is more than one C size Nickel-metal hydride battery or Nickel-cadmium battery connected in parallel.

13. The method of claim 1, wherein the electrolyte is tap water or an aqueous solution of a salt or baking soda.

14. The method of claim 13, wherein the container is made of an electrically conductive material to serve as the anode plate.

15. The method of claim 1, wherein a second container made of an electrically conductive material containing an electrolyte serves as a cathode plate and the user immerses a non-treated part of the anatomy into the second container.

16. The method of claim 15, wherein source of direct current power is pulse generator for generating the pulsed, monophasic voltage having an anode that is connected to anode plate and a cathode connected to an anode of a battery, and the cathode plate is connected to a cathode of the battery.

17. A method of building muscle and energizing skin cells through the use of electrochemistry comprising the steps of:
   immersing a part of the anatomy to be treated into a container containing an electrolyte of tap water or an aqueous solution of a salt or baking soda in contact with the anode of a pulse generator;
   placing another part of the anatomy in contact with a cathode plate connected to a cathode of a battery having an anode connected to a cathode of the pulse generator; and
   initiating the flow of current from the pulse generator to the container at a current amplitude of from about 1 to about 50 milliamperes, a voltage in the range of about 50 to about 120 volts of pulsed, monophasic voltage, a pulse duration in the range of about 0.2 to about 1 millisecond and at a frequency in the range of about 400 to about 1200 Hertz for treatment times in the range of about 5 minutes to about 15 minutes.

18. The method of claim 17, wherein the anode plate that is immersed in the electrolyte and the cathode plate is placed in contact with the other part of the anatomy outside of the electrolyte.

19. The method of claim 18, wherein the cathode plate is greater than 9 square inches in area, made of an easily corrodible metal, and covered with a wet, absorbent cloth.

20. The method of claim 17, wherein the container is made of an electrically conductive material to serve as the anode plate.

21. The method of claim 20, wherein a second container made of an electrically conductive material containing an electrolyte serves as a cathode plate and the user immerses another part of the anatomy into the second container.

22. A device for building muscle and energizing skin cells through the use of electrochemistry comprising:
   a power supply that produces a power signal at a power output terminal, the power signal having a current amplitude range variable between about 1 to about 50 milliamperes, and a DC voltage range from about 50 to about 120 volts;
   pulse generating circuitry operably connected to the power supply that operates to generate a pulse signal that has a pulse duration in the range of about 0.2 to about 1 millisecond, and a pulse frequency in the range variable between about 400 to about 1200 Hertz;
   a switching circuit that is coupled to receive the pulse signal, the switching circuit has a switching output terminal, and in response to the pulse signal, the switching circuit operates to couple and uncouple the switching output terminal to a system ground;
   cathode having a first end that is detachably attached to the switching output terminal and a second end;
   a battery whose anode is connected to the second end of the cathode and whose cathode is connected to a cathode plate;
   a container containing an electrolyte; and
   an anode having a first end that is detachably attached to the power output terminal, and a second end that comprises an anode plate in contact with the electrolyte, and wherein the muscle is built and the skin cells are energized by immersing a part of the anatomy to be treated into the container containing the electrolyte for a treatment time in the range of about 5 minutes to about 15 minutes.

23. The device of claim 22, wherein a pulsed monophasic waveform is generated by the device.

24. The device of claim 22, wherein the anode plate is immersed in the electrolyte in the container and the cathode plate is placed in contact with another part of the anatomy outside of the electrolyte.

25. The device of claim 22, wherein the container is made of an electrically conductive material to serve as the anode plate.

26. The device of claim 22, wherein a second container made of an electrically conductive material containing an electrolyte serves as a cathode plate into which the user immerses a non-treated part of the anatomy.

27. The device of claim 22, wherein the anode has a switch for turning the switching circuit on and off.

28. The device of claim 22, wherein the switching circuit is a CMOS 4538 solid state integrated circuit.

29. The device of claim 22, wherein the power signal is generated by a source of DC power.

* * * * *